US00PP16974P2

(12) United States Plant Patent
Utecht

(10) Patent No.: US PP16,974 P2
(45) Date of Patent: Aug. 8, 2006

(54) ***PELARGONIUM* PLANT NAMED 'FISROWEISS'**

(50) Latin Name: *Pelargonium×hortorum*
Varietal Denomination: Fisroweiss

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 29 days.

(21) Appl. No.: 11/167,676

(22) Filed: Jun. 27, 2005

(51) Int. Cl.
*A01H 5/00* (2006.01)

(52) U.S. Cl. ..... Plt./326

(58) Field of Classification Search ..... Plt./326
See application file for complete search history.

*Primary Examiner*—Kent Bell
(74) *Attorney, Agent, or Firm*—Jondle & Associates P.C.

(57) ABSTRACT

A new cultivar of *Pelargonium* particularly characterized by the combined features of large, pure-white, open, semi-double flowers, inflorescences high above the foliage, medium green and no zone to weakly zoned foliage, a vigorous growth, a round and bushy plant habit, and a mid-season flowering response is disclosed.

1 Drawing Sheet

Figure 1:
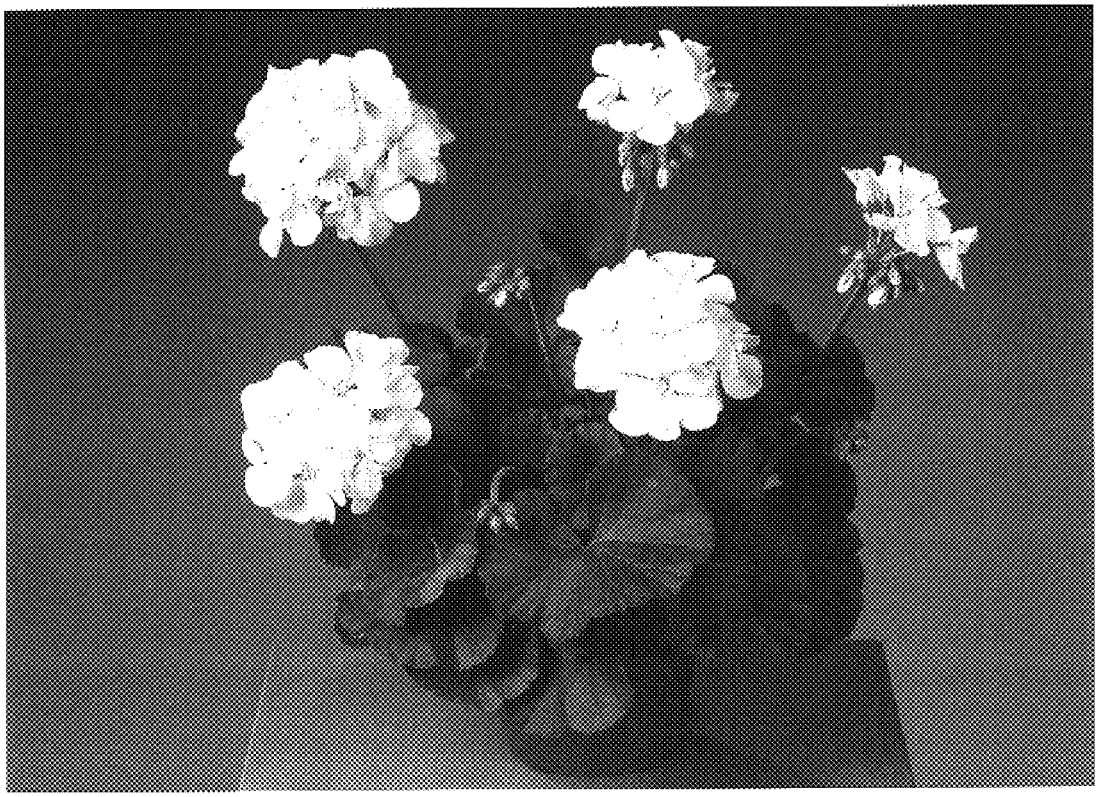

Genus and species: *Pelargonium×hortorum.*
Variety denomination: 'Fisroweiss'.

BACKGROUND OF THE NEW PLANT

The present invention comprises a new and distinct cultivar of *Pelargonium,* botanically known as *Pelargonium× hortorum,* a hybrid of *Pelargonium zonale* L'Héritier and hereinafter referred to by the cultivar name 'Fisroweiss'. The new cultivar is a product of a planned breeding program which had the objective of creating new varieties with white, semi-double flowers, intense green foliage and vigorous, but well-branched growth. 'Fisroweiss' was discovered as a seedling resulting from a cross between the female parent, 'North Star' (U.S. Plant Pat. No. 9,971), which has white semi-double flowers, rich flowering, medium green foliage without zonation and the male parent, hybrid seedling No. 93-735-11 (unpatented), which has white single-type flowers, dark green foliage with slight zonation, and fairly vigorous growth.

The new cultivar was created in 1995 in Hillscheid, Germany, and has been asexually reproduced repeatedly by vegetative cuttings in Galdar, Gran Canaria, Spain, and Hillscheid, Germany, over a nine-year period. 'Fisroweiss' has not been observed under all possible environmental conditions, thus, the phenotype may vary significantly with variations in the environment such as temperature, light intensity, and day length. It has been found to retain its distinctive characteristics through successive asexual propagations. 'Fisroweiss' reproduces true to type in successive generations of asexual reproduction.

Plant Breeder's Rights for this cultivar were applied for in Germany on Jun. 2, 2004. No sales or offers for sale of this cultivar were made before early July 2004.

SUMMARY OF THE INVENTION

The following are the most outstanding and distinguishing characteristics of this new cultivar when grown under normal commercial practices in Hillscheid, Germany.

1. Pure white, semi-double flowers;
2. Large inflorescences on strong peduncles well above the foliage;
3. Medium-green foliage, large leaves without or with only traces of zonation;
4. Tall and rounded bushy plant with vigorous growth;
5. A mid-season flowering response; and
6. Good stability of flower color and good rain resistance.

DESCRIPTION OF PHOTOGRAPH

This new geranium plant is illustrated by the accompanying photograph which shows blooms, buds, and foliage of the plant; the colors shown are as true as can be reasonably obtained by conventional photographic procedures. The photograph is of a twelve-week-old plant grown from rooted cuttings, in 14-cm pots, left un-pinched, and grown under greenhouse conditions which approximate those generally used in commercial practice.

FIG. 1 shows overall plant habit with blooms, buds, and foliage.

DESCRIPTION OF THE NEW CULTIVAR

The following detailed descriptions set forth the distinctive characteristics of 'Fisroweiss'. The data which define these characteristics were collected from asexual reproductions carried out in Hillscheid, Germany. The plant history was taken on twelve-week-old, un-pinched plants in 14-cm pots in a greenhouse during mid-May. The color readings were determined under natural light in mid-May from flowers grown in a greenhouse. Color references are to The R.H.S. Colour Chart of The Royal Horticultural Society of London (R.H.S.) (2001).

DETAILED BOTANICAL DESCRIPTION

Classification:

*Botanical.—Pelargonium×hortorum,* a hybrid of *Pelargonium zonale* L'Héritier.

*Common name.*—Geranium.

*Parentage.*—Female parent: 'North Star' (U.S. Plant Pat. No. 9,971). Male parent: Hybrid seedling No. 93-735-11 (unpatented).

Plant:

*Form.*—Shrub, self-branching, and rounded.

*Branching habit.*—8 branches per plant.

*Height.*—17.3 cm for a 9 week-old plant (measured from base of stem to the tips of the branches, excluding the inflorescences).

*Width.*—26.5 cm for 9 week-old plant.

*Time to produce a finished flowering plant.*—For spring flower response in Hillscheid, Germany, in 2004, 50% of the plants had open flowers after 8.5 weeks.

*Outdoor plant performance.*—Plants continuously flower; a flower count in mid-May of 2004 in Hillscheid, Germany indicated about 2–3 inflorescences per plant.

Leaves:

*Arrangement.*—Alternate.

*Immature leaf.*—Color: Upper surface: RHS 137D. Lower surface: RHS 137D.

*Mature leaf.*—Color: Upper surface: RHS 137C to RHS 137D (medium-green). Lower surface: RHS 137D. Length: 6.5 cm. Width: 10.3 cm.

*Zonation color.*—None to very weak RHS 137A (dark-green).

*Zonation diameter.*—Inner ring is 5.1 cm while ring of zonation is 2.0–2.5 cm wide (not always visible).

*Apex.*—Rounded.

*Base.*—Cordate.

*Shape.*—Kidney-shaped with very weak lobes and an open gap between the lowest lobes.

*Margin.*—Bi-crenate.

*Texture.*—Upper surface is dull and velvety.

Petioles:

*Length.*—6.0–7.0 cm.

*Diameter.*—0.3 cm.

*Color.*—RHS 143C (light-green).

*Texture.*—Covered with weak pubescence.

Stems:

*Length.*—7.0–9.0 cm.

*Internode length.*—1.5–2.0 cm.

*Color.*—RHS 143B (green).

*Texture.*—Appears smooth with slight pubescence.

Flower buds:

*Length.*—1.9 cm.

*Width.*—1.1 cm.

*Shape.*—Broad and elliptical.

*Color of sepals (just before petals unfold).*—RHS 144B (light-green).

*Color of petals (just before petals unfold).*—Mainly RHS 150D (white) to RHS 155A (cream).

Inflorescence:

*Type.*—An umbel composed of 20–30 flowers.

*Umbel diameter.*—9.6 cm.

*Umbel depth (height).*—6.3 cm.

*Umbel shape.*—Semi-spherical.

*Lastingness of umbel on the plant.*—About 18 days.

*Peduncle.*—Length: 17.4 cm. Diameter: 5.0 mm. Texture: Short pubescence. Color: RHS 143C (light-green).

*Pedicel.*—Length: 2.8 cm. Diameter: 1.0–2.0 mm. Texture: Weak with short pubescence. Color: RHS 144C (light-green).

Corolla:

*Diameter.*—5.4 cm.

*Form.*—Semi-double.

*Shape.*—Oval outline, wide open.

*Number of petals.*—6–9.

*Number of petaloids.*—1–3, narrower and shorter than the petals.

*Petaloid color.*—RHS 155D (white) for both upper and lower surfaces.

*Lastingness of individuals flowers on the plant.*—8–9 days at 18° C.

*Fragrance.*—None.

Petals:

*Upper petals.*—Length: 2.8–3.2 cm. Width: 2.1–2.5 cm. Color: Upper surface: Lighter than RHS 155D (white). Lower surface: Lighter than RHS 155D (white) and uniform. Markings: Small RHS 56B (light-pink) veins at the base.

*Lower petals.*—Length: 3.0–3.2 cm. Width: 2.3–2.5 cm. Color: Upper surface: Lighter than RHS 155D (white). Lower surface: Lighter than RHS 155D (white) and uniform. Markings: Absent.

*Shape.*—Obovate.

*Apex.*—Rounded.

*Base.*—Attenuate.

*Margin.*—Mainly entire or slightly crenated at the tips.

*Texture.*—Smooth, glabrous, and slightly glossy.

Sepals:

*Number.*—5, occasionally an incomplete $6^{th}$ sepal is found.

*Length.*—1.0–1.1 cm.

*Width.*—0.4–0.5 cm for the largest upper sepal and 0.3 cm for the other sepals.

*Shape.*—Linear to lanceolate.

*Apex.*—Acute.

*Margin.*—Entire.

*Base.*—Truncate.

*Texture.*—Very weak pubescence.

*Color.*—RHS 144A (light-green) to RHS 144B (light-green) for both upper and lower surfaces.

Reproductive organs:

*Androecium.*—Number of anthers: Often fertile 5–7 anthers. Filament color: RHS 155D (white). Filament length: 7.0–8.0 mm. Pollen color: RHS 28A (yellow-orange). Pollen amount: Abundant.

*Gynoecium.*—Pistil number: 1. Pistil length: 8.0 mm. Stigma color: RHS 155A (white). Stigma shape: 5–6 lobed. Style color: RHS 155A (white). Style length: 3.0–4.0 mm. Style shape: Filament-like with the lobes of the stigma at right angles.

Fruit/seed set: No seed set observed.

Disease and insect resistance: Moderately resistant to *Botrytis.*

COMPARISON WITH KNOWN CULTIVARS

Of the many commercial cultivars known to the present inventor, the most similar in comparison to 'Fisroweiss' are the varieties 'Fisrowi' (U.S. Plant Pat. No. 12,389) and the variety 'North Star' (U.S. Plant Pat. No. 9,971).

Cultivar 'Fisroweiss' differs from the female parent 'North Star' (U.S. Plant Pat. No. 9,971) in that the inflorescences and leaves of 'Fisroweiss' are larger and the plant habit is in general, much taller.

Cultivar 'Fisroweiss' differs from the male parent hybrid seedling No. 93-735-11 (unpatented), in that 'Fisroweiss' has semi-double flowers with 7–9 petals, and medium green foliage, while the male parent hybrid seedling no. 93-735-11 has single-type flowers with 5 petals, and dark green leaves.

Cultivar 'Fisroweiss' differs from the commercial comparison variety 'Fisrowi' (U.S. Plant Pat. No. 12,389) in that 'Fisroweiss' is somewhat taller, has slightly smaller umbels, and is more floriferous. The foliage of 'Fisroweiss' appears to be a slightly deeper green and the leaves are somewhat smaller. Additionally, a typical characteristic of 'Fisroweiss' is that it has tiny light-pink veins at the bases of its upper petals while 'Fisrowi' does not.

I claim:

1. A new and distinct cultivar of *Pelargonium* plant as shown and described herein.

* * * * *